US005147929A

United States Patent [19]

Blankemeyer-Menge et al.

[11] Patent Number: 5,147,929
[45] Date of Patent: Sep. 15, 1992

[54] PROCESS FOR MILD ESTERIFICATION OF A CARBOXYLIC ACID WITH AN ALCOHOL COMPONENT

[75] Inventors: Birgit Blankemeyer-Menge; Ronald Frank, both of Braunschweig, Fed. Rep. of Germany

[73] Assignee: Gesellschaft fur Biotechnologische Forschung GmbH, Braunschweig, Fed. Rep. of Germany

[21] Appl. No.: 574,456

[22] Filed: Aug. 29, 1990

[30] Foreign Application Priority Data

Aug. 29, 1989 [DE] Fed. Rep. of Germany ....... 3928564

[51] Int. Cl.$^5$ ................... C08F 283/00; C08C 229/08; C08C 67/08
[52] U.S. Cl. ................... 525/54.11; 525/434; 560/155; 560/265
[58] Field of Search ...................... 525/54.11; 560/155

[56] References Cited

PUBLICATIONS

Ronald Frank and Renate Doring, "Simultaneous Multiple Peptide Synthesis Under Continuous Flow Conditions on Cellulose Paper Disc as Segmental Solid Supports", Tetrahedron 44, 6031–6040, 1988.

*Primary Examiner*—Joseph L. Schofer
*Assistant Examiner*—Wu C. Cheng
*Attorney, Agent, or Firm*—Kane, Dalsimer, Sullivan, Kurucz, Levy, Eisele and Richard

[57] ABSTRACT

The invention relates to a process for mild esterification of a sensitive carboxylic acid, in particular a suitably protected amino acid, with an alcohol component, the esterification according to the invention being carried out in the presence of 2,4,6-mesitylene-1-sulfonyl-3-nitro-1,2,4-triazolide (MSNT) and a weak base in an aprotic and non-basic solvent.

6 Claims, No Drawings

PROCESS FOR MILD ESTERIFICATION OF A CARBOXYLIC ACID WITH AN ALCOHOL COMPONENT

The vast number of natural substances, such as antibiotics, alkaloids, proteins/peptides, coenzymes, lipids, saccharides/oligosaccharides, nucleic acids, terpenoids, steroids and vitamins, are complex, multifunctional organic compounds, i.e. their molecular structure has, next to one another, several groups of atoms of the same, similar and/or different reactivity. The chemical synthesis or modification of such natural substances nearly always requires the regioselective reaction of such a group in the presence of the other groups without the total or partial structure of the remainder of the molecule being changed or destroyed.

The process according to the invention described below was developed in order to react a carboxylic acid group (carboxyl group=—COOH) with an alcohol component to give an ester under very mild conditions, in order to be able to react sensitive or unstable carboxylic acids with alcohols which may be sensitive or unstable in a satisfactory manner. The process is illustrated by way of example for the chemical synthesis of peptides from suitably protected amino acid derivatives.

Amino acids are, in general, chemical compounds which contain an amino group (—NH$_2$), a carboxyl group (—COOH) and optionally also any other additional chemical groups ($R_n$) desired. A specific group of amino acids are the natural (so-called essential) amino acids in which the amino and carboxyl group are in the α-position and the chiral α-C atom is present exclusively in the L-configuration. If the amino group and optionally the other side groups in amino acids are blocked in their chemical reactivity by so-called protecting groups, such an amino acid derivative can be esterified with an alcohol component in a controlled manner via the still free carboxyl group. Thus, for example, the protection of the carboxyl function of the carboxy-terminal amino acid, i.e. the first peptide building block, by esterification with an alcohol derivative is a fundamental step for the chemical synthesis of peptides. In the modified solid-phase synthesis according to Merrifield (JACS, 85 (1963) 2149) predominantly carried out today, a suitable support material is used as the C-terminus protection. Such a support material is often chemically derivatized or modified in such a way that on its surface it carries hydroxyl groups with which suitably protected amino acids can be linked. For the first two building blocks, the peptide synthesis may be illustrated by the following scheme.

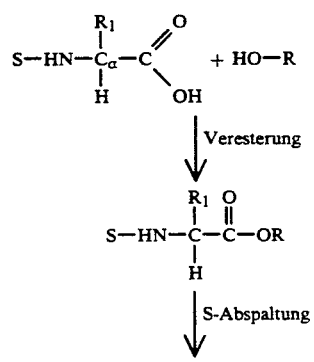

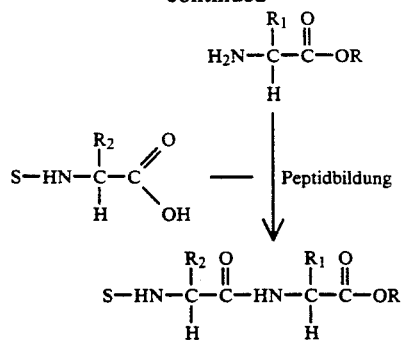

The known esterification requires mild reaction conditions, as many protected amino acid derivatives are fairly unstable. Various methods can be taken from the literature; cf. J. Chem. Soc. Chem. Commun., (1981) 336; Tetrahedron Lett., 28 (1987) 6147; Liebigs Ann. Chem., (1987) 1031; and Int. J. Peptide Protein Res., 33 (1989) 386. However, these known methods are often accompanied by side reactions or often give unsatisfactory yields. The usual side reactions occur if strong bases, for example pyridine or dimethylaminopyridine (DMAP), are employed as catalysts. For example, it is not possible to use the process known from Tetrahedron, 36 (1980) 3075-3085, in which a phosphoric acid derivative is esterified in the presence of 2,4,6-mesitylene-1-sulfonyl-3-nitro-1,2,4-triazolide (MSNT) in pyridine as a solvent, for the esterification of sensitive carboxylic acids, such as amino acids. The sensitivity of amino acids is thus expressed in dipeptide formation as a result of instability of the protecting group S (for example fluorenylmethoxycarbonyl (Fmoc)) and racemization at the chiral Ca atom of the amino acid. An improvement to the known methods is therefore desirable.

To this end, a process for mild esterification of a carboxylic acid with an alcohol component in the presence of 2,4,6-mesitylene-1-sulfonyl-3-nitro-1,2,4-triazolide (MSNT) and a base is provided according to the invention, which comprises carrying out the esterification in the presence of N-methylimidazole (MeIm) in an aprotic and non-basic solvent.

An alcohol component is to be understood as meaning lower molecular weight components, such as protecting groups, and high molecular weight components, such as soluble supports or solid-phase supports. In this connection and for the suitable protection of amino acids, compare Wünsch et al. in: Heuben-Weyl, Methoden der org. Chemie (Methods of Organic Chemistry), 4th edition, Volume 15, Thieme-Verlag, Stuttgart 1974. For hydroxyl group-containing supports, reference can be made to the prior art.

For example, a suitably protected amino acid, in particular an amino acid having a protected amino group in the α-position, can be esterified.

According to specific embodiments, the amino acid is used in the form of one of its enantiomers or of a natural amino acid. The process according to the invention can be illustrated for this embodiment by the following scheme:

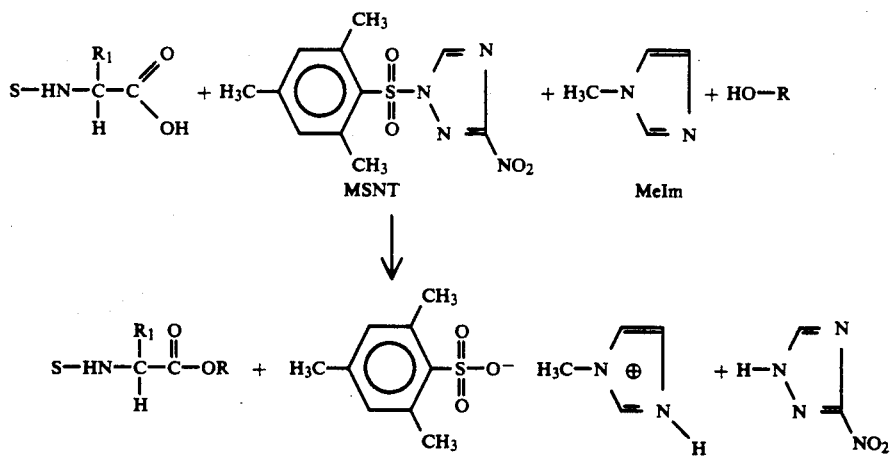

The process according to the invention can be carried out in dichloromethane, chloroform or THF as solvent.

For example, the process according to the invention can be carried out at a molar ratio of amino acid:MSNT:MeIm such as 1: about 1: up to about 1 and preferably up to about 0.75.

The invention is illustrated below in more detail by examples.

EXAMPLE 1 AND COMPARISON EXAMPLE 1

DCC=dicyclohexylcarbodiimide
DMAP=dimethylaminopyridine
Fmoc=fluorenylmethoxycarbonyl
MeIm=N-methylimidazole
MSNT=2,4,6-mesitylene-1-sulfonyl-3-nitro-1,2,4-triazolide
NMM=N-methylmorpholine
1 eq=mmol of OH functions of amount of support material employed Various αN-Fmoc-protected amino acid derivatives were esterified with cellulose (support material) which was derivatized with p-alkoxybenzyl alcohol; Frank & Döring, Tetrahedron, 44 (1988) 6031–6040. The results obtained by the process according to the invention can be taken from the following table, column A (Example 1).

The experiments according to the invention were additionally compared with the prior art; J. Chem. Soc. Chem. Commun., (1981) 336. To this end, these amino acids were linked with the abovementioned derivatized cellulose using dicyclohexylcarbodiimide (DCC) as condensing agent and dimethylaminopyridine (DMAP) and N-methylmorpholine (NMM) as bases, as this standard reaction is the most common method of the prior art. The results can be taken from the following Table 1 column B (Comparison Example 1).

TABLE 1

| Amino acid derivative | A MSNT/MeIm Yield [%] | A MSNT/MeIm Racemate [%] | B DCC/DMAP/NMM Yield [%] | B DCC/DMAP/NMM Racemate [%] |
|---|---|---|---|---|
| Fmoc Asp(tBu) | 53 | 1.7 | 52 | 2.8 |
| Fmoc Cys(tBu) | 76 | 2.3 | 65 | 11.6 |
| Fmoc Phe | 68 | 0.7 | 69 | 2.0 |
| Fmoc Trp | 74 | <0.2 | 63 | 0.8 |
| Fmoc Ile | 48 | <0.2 | 26 | 3.0 |
| Fmoc Lys(Boc) | 72 | <0.2 | 44 | 1.0 |

A: 2 eq. of amino acid derivative
  2 eq. of MSNT

TABLE 1-continued 1.5 eq. of MeIm
in dichloromethane/tetrahydrofuran
30 min at room temperature
B: 2 eq. of amino acid anhydride (prepared in situ from
4 eq. of amino acid derivative and 2 eq. of DCC)
0.1 eq. of DMAP
1 eq. of NMM
in dimethylformamide
30 min at room temperature It can be inferred from the table that comparably good or better yields and a clearly lower rate of racemization can be achieved according to the invention.

If 4 eq. of amino acid derivative, which corresponds to an identical consumption of protected amino acid, are used in the process according to the invention and in the prior art method, yields of 80 to 100% can be achieved.

EXAMPLE 2 AND COMPARISON EXAMPLE 2

The experiments, according to the invention, of Example 1 were repeated with the exception that similarly derivatized polystyrene was used instead of the derivatized cellulose, equally good results being obtained. For the support see Wang, JACS, 95 (1973) 1328–1333. The results can be taken from Table 2 (A: Example 2; B: Comparison Example 2).

TABLE 2

| Amino acid derivative | A MSNT/MeIm Yield [%] | A MSNT/MeIm Racemate [%] | B DCC/DMAP/NMM Yield [%] | B DCC/DMAP/NMM Racemate [%] |
|---|---|---|---|---|
| Fmoc Asp(tBu) | 65 | not determined | 49 | not determined |
| Fmoc Phe | 59 | not determined | 55 | not determined |
| Fmoc Ile | 55 | not determined | 49 | not determined |

A: 2 eq. of amino acid derivative
  2 eq. of MSNT
  1.5 eq. of MeIm
  in dichloromethane/tetrahydrofuran
  30 min at room temperature
B: 2 eq. of amino acid anhydride (prepared in situ from
  4 eq. of amino acid derivative and 2 eq. of DCC)
  0.1 eq. of DMAP
  1 eq. of NMM
  in dimethylformamide
  30 min at room temperature

COMPARISON EXAMPLES 3 TO 4 AND EXAMPLES 3 TO 4

Fmoc-Leu-OH (AA) was esterified with cellulose, which was loaded with alkoxybenzyl alcohol, in the presence of 1-mesitylenesulfonyl-3-nitro-1,2,4-triazole (MSNT) in methylene chloride with the aid of pyridine (Comparison Examples 3 and 4) and 1-methylimidazole (MeIm). Details and the reaction times and yields can be taken from the following table:

| Example | Comparison Example | Fmoc-Leu-OH [eq.*] | MSNT [eq.*] | Base [eq.*] | RZ [min] | Yield [μmol/F.] | [%*] |
|---|---|---|---|---|---|---|---|
|   | 3 | 5 | 5  | 20 pyridine | 30 | 1.8 | 23 |
| 3 |   | 5 | 5  | 20 MeIm     | 15 | 6.7 | 84 |
|   | 4 | 5 | 10 | 20 pyridine | 30 | 2.8 | 35 |
| 4 |   | 5 | 10 | 20 MeIm     | 15 | 7.2 | 90 |

*Based on the alkoxybenzyl alcohol loading of the cellulose employed

Examples 3 and 4 illustrate that MeIm is a very much better base than, for example, pyridine.

We claim:

1. A process for mild esterification of a carboxylic acid with an alcohol component in the presence of 2,4,6-mesitylene-1-sulfonyl-3-nitro-1,2,4-triazolide (MSNT) and a base, which comprises carrying out the esterification in the presence of N-methylimidazole (MeIm) in an aprotic and non-basic solvent.

2. The process as claimed in claim 1, wherein the acid is esterified using a solid-phase support carrying hydroxyl groups.

3. The process as claimed in claim 1, wherein a suitably protected amino acid, in particular an amino acid having a protected amino group in the α-position, is esterified.

4. The process as claimed in claim 1, wherein the amino acid is employed in the form of one of its enantiomers or wherein a natural amino acid is employed.

5. The process as claimed in claim 1, wherein esterification is carried out in dichloromethane, chloroform or THF as solvent.

6. The process as claimed in claim 1, wherein the reaction is carried out at a molar ratio of amino acid:MSNT:MeIm such as 1: about 1: up to about 1 and preferably up to about 0.75.

* * * * *